(12) United States Patent
Allred et al.

(10) Patent No.: US 8,092,024 B2
(45) Date of Patent: Jan. 10, 2012

(54) EYE MEASUREMENT APPARATUS AND METHODS OF USING SAME

(75) Inventors: Lloyd G. Allred, Rochester, NY (US); Jeffrey B. McBeth, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 149 days.

(21) Appl. No.: 12/264,965

(22) Filed: Nov. 5, 2008

(65) Prior Publication Data
US 2010/0110380 A1 May 6, 2010

(51) Int. Cl.
*A61B 3/10* (2006.01)
*A61B 3/00* (2006.01)

(52) U.S. Cl. ........................................ 351/214; 351/205
(58) Field of Classification Search .................. 351/200, 351/205, 206, 214
See application file for complete search history.

(56) References Cited

U.S. PATENT DOCUMENTS

| | | | |
|---|---|---|---|
| 4,400,070 A * | 8/1983 | Isono et al. .................. 351/208 |
| 5,512,965 A | 4/1996 | Snook | |
| 5,512,966 A | 4/1996 | Snook | |
| 6,286,958 B1 | 9/2001 | Koest | |
| 6,575,573 B2 | 6/2003 | Lai | |
| 6,692,126 B1 | 2/2004 | Xie | |
| 2007/0188709 A1 | 8/2007 | Saarloos | |

OTHER PUBLICATIONS

Geometric Transformations, printed Sep. 15, 2009 http:/cse.taylor/edu/~btoll/s99/424/res/mtu/Notes/geometry/geo-tran.htm.
Homography, http://en.wikipedia.org/wiki/homography, printed Oct. 12, 2010, 4 pages.

* cited by examiner

*Primary Examiner* — James Greece
(74) *Attorney, Agent, or Firm* — Jeffrey Powers

(57) ABSTRACT

An apparatus for measuring a subject's eye having an instrument axis, comprising a slit projector for projecting slits of light, at least one sensor. The apparatus being adapted to form a first image of light from a first slit on the at least one sensor after the light scatters from the eye along a first pathway. The apparatus adapted to form a second image of light from the first slit on the at least one sensor after the light scatters from the eye along a second pathway. The apparatus comprising a processor operatively coupled to receive the first image and the second image, the processor adapted to perform a projective transformation of the second image and to combine data from the first image and the second image, after it is transformed, to form a third image.

7 Claims, 7 Drawing Sheets

EYE MEASUREMENT APPARATUS AND METHODS OF USING SAME

FIELD OF INVENTION

The present invention relates to eye measurement apparatus and methods of using the same, and more particularly to an eye measurement apparatus providing images having the effects of specular reflection reduced.

BACKGROUND OF THE INVENTION

Ophthalmologists and optometrists would like to have accurate representations of portions of subjects' eyes. Such representations include, for example, representations of a subject's corneal surfaces, corneal thickness, corneal density and lens surfaces. This information may be used, for example, to prescribe contact lenses, intraocular lenses and eye glasses, and to reshape the cornea by surgical procedures or to perform other surgical procedures. Since it is not comfortable to measure these data by physically contacting an eye, remote sensing techniques are preferably used to obtain the representations.

One common technique for obtaining representations of eyes includes projecting narrow bands of light (commonly referred to as slits or slit beams) onto a subject's cornea at multiple locations on the cornea. For each of the slits, after the light in the slit has been scattered by the eye, an image of a cross section of the eye is obtained using the scattered light. Images from tens of slit projections (e.g., approximately 40 slits of light at different locations) are used to construct representations of one or more portions of the subject's eye.

FIGS. 1 and 2 illustrate one type of measurement apparatus 100 in which slits of light S, S', at various angular deviations (a) about an instrument axis 102, are projected. The slits impinge on multiple locations on a cornea C. FIG. 2 is a view of apparatus 100 taken along line 2-2 of FIG. 1. Light scattered by the eye from each slit permits a cross section of the eye to be obtained; and multiple cross sections from slits of different angular deviations permit two-dimensional or three-dimensional representations of the eye to be constructed.

To produce slits of light S, S', a projector 122 having a long, thin aperture 110 (having a length extending in the Y direction in FIG. 1) placed in front of a source 120 projects slits of light onto a beam splitter (or mirror) 125 which directs the light onto cornea C and lens L along instrument axis 102. To achieve slits of light S and S' at the various angular deviations, apparatus 100 (including all components therein) and a portion 170a of the front faceplate 170 of the apparatus are rotated about instrument axis 102. After the light is scattered by the eye, the scattered light re-enters the apparatus through a camera port 135 and is imaged by a camera 142 comprising a lens 130 and a CCD sensor 140. The light gathered by lens 130 is projected onto CCD sensor 140. One image is obtained for each of a plurality of rotational positions of the apparatus.

Although camera 142 and slit projection optics are arranged so that camera 142 receives diffuse scattering of light, a troublesome affect occurs when spurious portions of slit light are specularly reflected from the eye and are received by the camera. For example, such specular reflections may occur due to the structure of cells in an eye or due to the topography of a surface of the eye.

SUMMARY

According to aspects of the invention, two images of a same slit of light are obtained from two different perspectives (i.e., along two different pathways). Typically, if one of the images is afflicted by specular reflection, in one or more particular regions of an image the other will not be so afflicted. The Applicants have also determined that, although the images are not directly related after acquisition (because they are from different perspectives), a perspective transform can be performed on at least one of the images. Accordingly, pixels corresponding to one another can be determined, compared, and, in the event that specular reflection is present, a pixel from one of the images selected so as to obviate or ameliorate the problems of specular reflection. In such a manner, two images can be combined to reduce the effects of specular reflection.

An aspect of the invention is directed to an apparatus for measuring a subject's eye having an instrument axis, comprising a slit projector for projecting slits of light, at least one sensor, and a processor. The apparatus is adapted to form a first image of light from a first slit on the at least one sensor after the light scatters from the eye along a first pathway, and the apparatus adapted to form a second image of light from the first slit on the at least one sensor after the light scatters from the eye along a second pathway. The processor is operatively coupled to receive the first image and the second image, and adapted to perform a projective transformation of the second image and to combine data from the first image and the second image, after it is transformed, to form a third image.

In some embodiments, the at least one sensor comprises (A) a first sensor, the apparatus adapted to form the first image on the first sensor using light scattered along the first pathway, and (B) a second sensor, the apparatus adapted to form the second image on the second sensor using light scattered along the second pathway.

In some embodiments, a second slit of the plurality of slits is projected at a different angle than the first slit. The apparatus is adapted to form a fourth image of light from the second slit on the at least one sensor after the light scatters from the eye along a third pathway, and the apparatus is adapted to form a fifth image of light from the second slit on the at least one sensor after the light scatters from the eye along a fourth pathway. In such embodiments, the processor is operatively coupled to receive the fourth image and the fifth image. The processor is adapted to perform a projective transformation of the fourth image, and the processor is adapted to combine data from the fourth image (after it is transformed) and the fifth image to form a sixth image.

In some embodiments, the at least one sensor comprises a single sensor, and the apparatus comprises steering optics adapted to form the first image on the single sensor using light scattered along the first pathway, and the apparatus is adapted to form the second image on the single sensor using light scattered along the second pathway.

In some embodiments, in addition to transforming the second image, the processor is adapted to perform a projective transformation of the first image prior to formation of the third image.

In some embodiments, a second slit of the plurality of slits is positioned so as to be translated without angular deviation relative to the first slit. In such embodiments, the apparatus is adapted to form a fourth image of light from the second slit on the at least one sensor after the light scatters from the eye along a third pathway, and the apparatus is adapted to form a fifth image of light from the second slit on the at least one sensor after the light scatters from the eye along a fourth pathway. The processor operatively coupled to receive the fourth image and the fifth image, and to perform a projective transformation of the fourth image, and to combine data from the fourth image, after it is transformed, and the fifth image to form a sixth image.

In some embodiments, the apparatus is adapted to acquire multiple cross sectional images formed using light from the plurality slits, and the processor is adapted to form a multi-dimensional representation of the eye from the multiple cross sectional images, wherein at least one of the cross sectional images is the third image.

Another aspect of the invention is direct to a method for measuring a subject's eye having an instrument axis. The method comprises projecting a first slit of light onto the subject's eye, forming a first image along a first pathway using light from the first slit, after the light is scattered form the eye, and forming a second image along a second pathway using light from the first slit, after the light is scattered form the eye. The method comprises performing a projective transformation of one of the images (e.g., the second image) and combining data from the first image and the second image to form a third image.

In some embodiments, the step of combining comprises comparing an intensity of a first pixel from the first image and an intensity of a second pixel from the second image to determine if the pixel intensities are different by more than a factor. After comparing, the one of the first pixel and the second pixel that has a lesser intensity is selected for use in the third image.

In some embodiments, the step of forming the first image comprises forming the first image on a first sensor using light scattered along the first pathway, and forming the second image on a second sensor using light scattered along the second pathway.

In some embodiments, the method comprises a step of projecting a second slit of light onto the subject's eye at a different angle than the first slit. The method also includes forming a fourth image along a third pathway using light from the second slit, after the light is scattered form the eye, and forming a fifth image along a fourth pathway using light from the second slit, after the light is scattered form the eye. The method also includes performing a projective transformation of the fourth image; and combining data from the fourth image, after the step of performing a projective transformation, with data from the fifth image to form a sixth image.

In some embodiments, the step of forming the first image comprises forming the first image on a first of the at least one sensors using light scattered along the first pathway, and the step of forming the second image comprises forming the second image on the first of the at least one sensors using light scattered along the second pathway.

In some embodiments, in addition to transforming the second image, the method comprises performing a projective transformation of the first image, prior to the step of combining.

In some embodiments, the method comprises a step of projecting a second slit of light onto the subject's eye, the second slit being translated without rotation, relative to first slit. The method also comprises forming a fourth image along a third pathway using light from the second slit, after the light is scattered form the eye; and forming a fifth image along a fourth pathway using light from the second slit, after the light is scattered form the eye. The method also comprises performing a projective transformation of the fourth image, and combining data from the fourth image (after the step of performing a projective transformation) and the fifth image to form a sixth image.

In some embodiments, the method further comprises acquiring multiple cross sectional images each corresponding to a corresponding one of a plurality slits, and forming a multidimensional representation of the eye using the multiple cross sectional images, wherein at least one of the cross sectional images is the third image.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which.

DETAILED DESCRIPTION

Aspects of the present invention are directed to an eye measurement apparatus adapted to project slits of light at different positions on an eye and adapted to reduce the affects of specular reflection on images obtained by the apparatus. The apparatus comprises at least one camera. The apparatus is adapted such that the at least one camera forms a first image along a first pathway and a second image along a second pathway. The images are formed using light from the slits of light after the light scatters from the eye. A processor is coupled to receive the first and second images, and is adapted to perform a projective transformation of at least one of the first image and the second image, and to combine data from the first image and the second image to form a third image in which the effects of specularly reflected light are reduced or eliminated.

Figure 1:
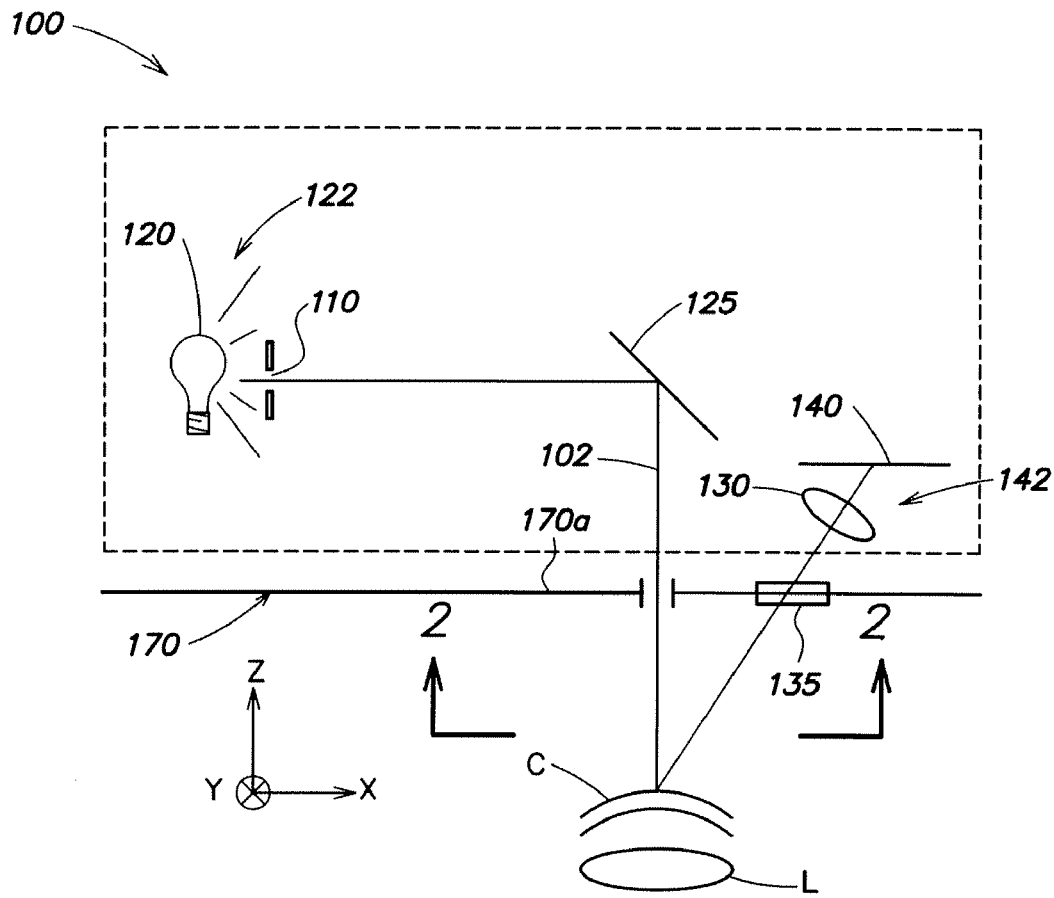
FIG. 1 is a schematic view of a prior art eye measurement apparatus illustrating optical layout.
Figure 2:
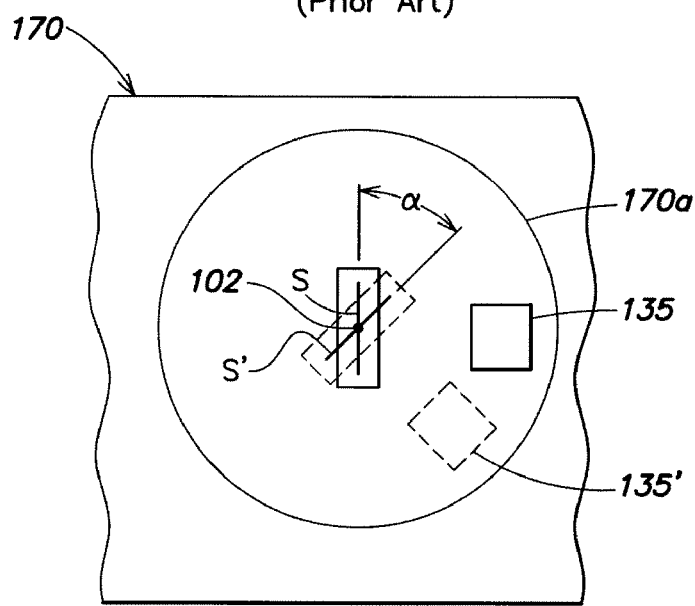
FIG. 2 is a schematic view of the front of the apparatus of FIG. 1 taken along line 2-2 of FIG. 1 illustrating the arrangement of the projected slits and the slit camera port.
Figure 3:
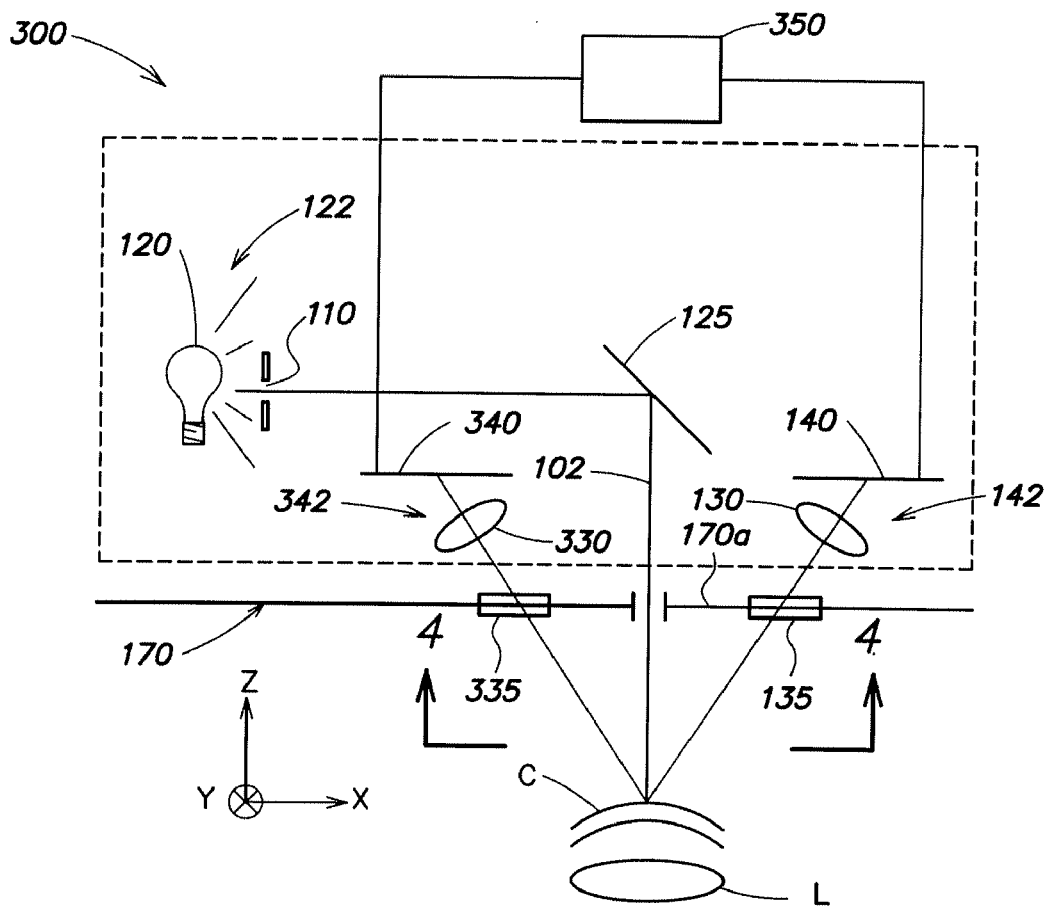
FIG. 3 is a schematic view of an example embodiment of a measurement apparatus including a first camera and a second camera according aspects of the present invention.
Figure 4:
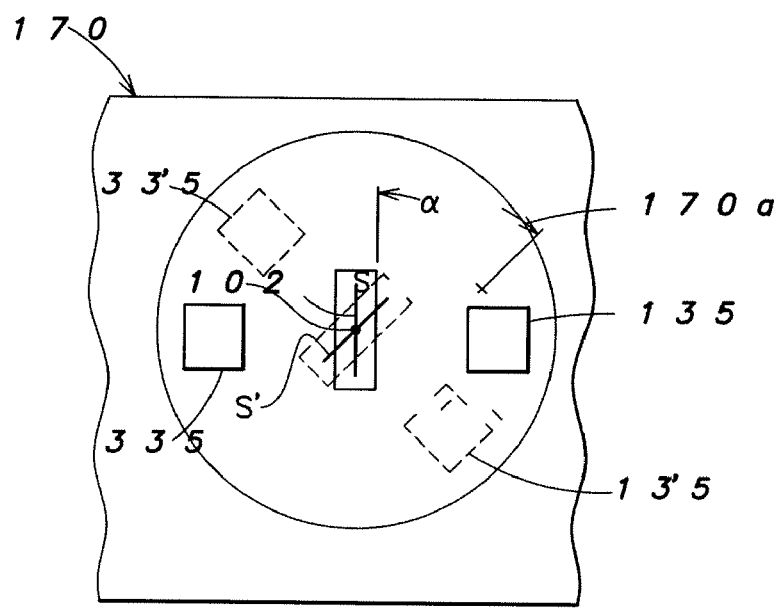
FIG. 4 is a schematic view of the front of the apparatus of FIG. 4 taken along line 4-4 of FIG. 3 illustrating slits projected at multiple angles and corresponding positions of the first camera port and the second camera port.

FIGS. 3 and 4 illustrate an example of a measurement apparatus 300 comprising a slit projector 122 for projecting slits of light, and cameras 142 and 342. Slit projector 122 projects slits of light S, S' at various angular deviations (a) about an instrument axis 102 (i.e., the slits are projected such that the slits impinge on multiple locations on a cornea C). Apparatus 300 is the same as apparatus 100 in FIG. 1 except that, in addition to camera 142 which images along a first pathway (i.e., from a first perspective), a second camera 342 is included to from a second image along a second pathway (i.e., from a second perspective) and both cameras are operatively coupled to a processor 350 that is programmed to combine the images in a manner that reduces the effects of specular reflection. Like camera 142, camera 342 is configured such that after a slit of light is scattered by the eye, the scattered light enters the apparatus through a second camera port 335 and is imaged by camera 342 along the second pathway and onto an image sensor 340. The second camera comprises a lens 330 and a CCD sensor 340. The light gathered by lens 330 is projected onto CCD sensor 340. The images obtained are cross sections corresponding to different slit locations. Apparatus 300 is configured such that, for at least some slit positions, images of the eye are obtained by both camera 142 and camera 342. In some embodiments, an image is obtained from both of cameras 142 and 342 for all slit projections.

FIG. 4 is a schematic view of the front of the apparatus of FIG. 3 taken along line 4-4 illustrating slits S and S' projected at two different angles (i.e., they are non-parallel). FIG. 4 shows port 135 (which leads to first camera 142 (shown in FIG. 3)) and port 335 (which lead to second camera 342 (shown in FIG. 3)) in positions that correspond to the first slit angle; and ports 135' and 335' designate ports 135 and 335 when they are rotated to positions corresponding to the second slit angle. As described above, for at least some slit positions, light scattered by the eye is captured by both camera 142 and camera 342. It will be appreciated that, for a given position, it is generally preferred that the first image and the second image are obtained at the same time or at very nearly the same time to avoid excessive movement of the eye between the capture of the two images. It will be appreciated that the pathways along which light from slit S is imaged are different than the pathways along which light from slit S' is imaged.

As described in greater detail below, for slit positions where both cameras capture an image, processor 350 receives the images from sensors 140 and 340 and performs a projective transformation of at least one of the first image (e.g., the image captured by first camera 142) and second image (e.g., the image captured by second camera 342). Also, as described in greater detail below, data from the first image and the second image is combined to form a third image, after the transformation. It will be appreciated that a given image that has been transformed is referred to, herein, simply as the given image after transformation. For example, the first image after it has been transformed may be referred to as "the first image after transformation" or the "the first image after it is transformed" or a similar designation.

Figure 5:
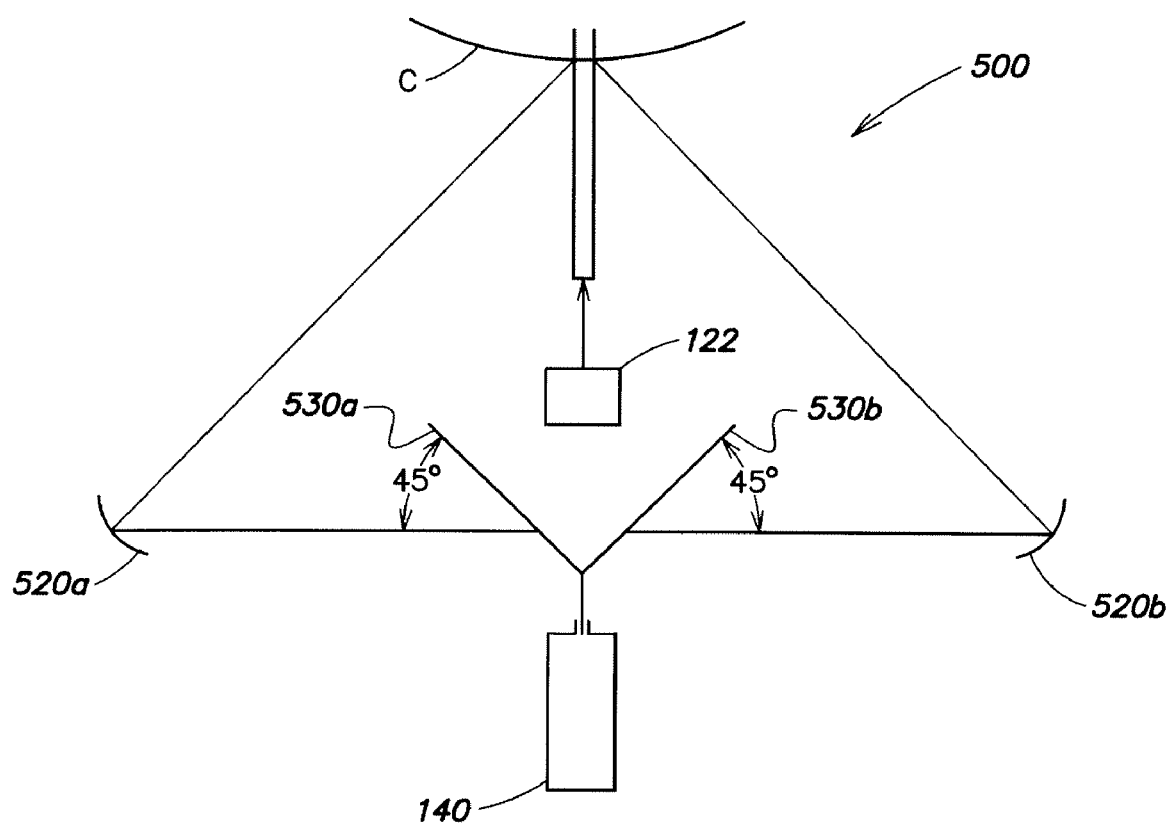
FIG. 5 is an illustration of an example of an apparatus configured with a single camera, and mirrors configured to provide images of light along different pathways (i.e., from different perspectives)

Although apparatus 300 comprises two cameras with the cameras adapted to form images of the eye along different pathways (i.e., from different perspectives), as shown in FIG. 5, an apparatus 500 can be configured with a single camera 140, and steering optics (e.g., mirrors 520*a* and 520*b* configured to provide optical power, steering mirrors 530*a* and 530*b*, and/or beam splitters (not shown)) configured to provide images along different pathways, using scattered light from slits provided by projector 122.

Figure 6A:
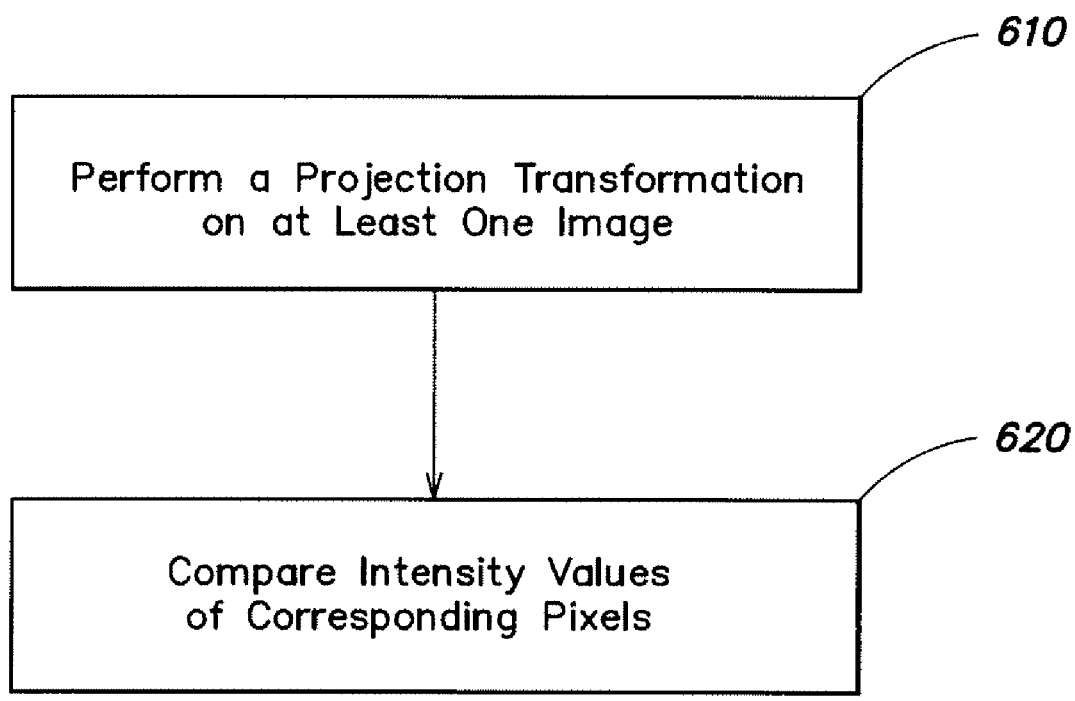
FIGS. 6A and 6B are flow charts describing techniques for processing two camera images to form a single image have reduced specular reflection according to aspects of the present invention.

Combining the first and second images obtained from different perspectives to form a single image will be described below with reference to FIGS. 6A and 6B. In some embodiments, combining the first image and the second image occurs on a pixel-by-pixel basis to form the third image. It will be understood that as used herein the term "pixel-by-pixel" refers to pixels of the image. Pixels of an image may comprise one or more pixels of an image sensor (e.g., CCD 140 or 340).

As described below, pixels in the two images can be combined in a number of different manners to form a single image having reduced or eliminated specular reflection. According to aspects of the invention pixels, that are affected by specular reflection are identified and eliminated. To identify pixels, affected by specular reflection, intensity levels of corresponding pixels in the first and second images are compared (step 620). The term "corresponding pixels" means pixels containing image information of a common portion of an eye. Since the images are obtained at two different perspectives, as shown in step 610 typically a projective transform is performed on at least one of the images prior to comparison (step 610) such that the images correspond to a common perspective.

Figure 6B:
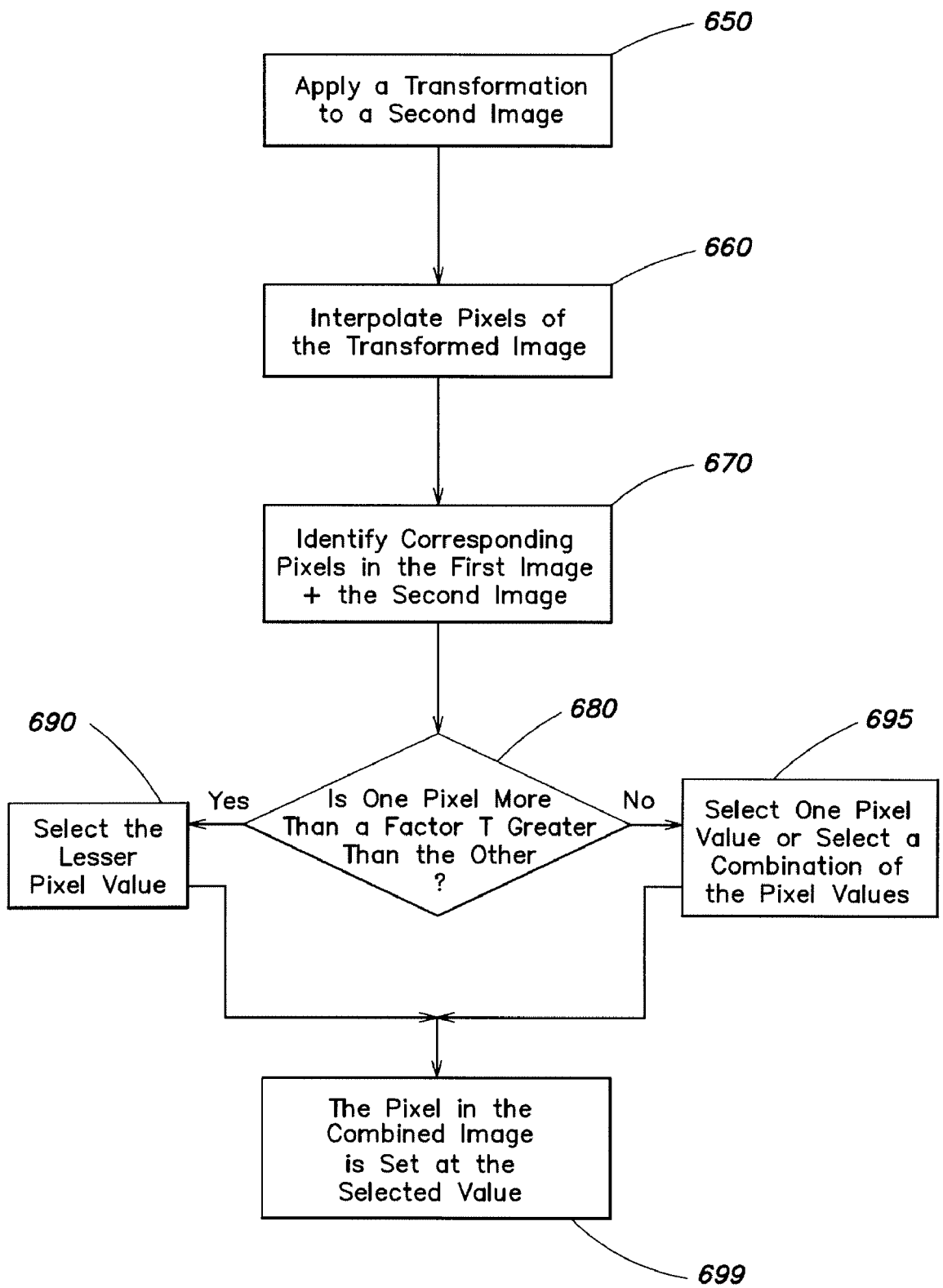

FIG. 6B is a flow chart showing further detail of examples of the transformation (i.e., application of a transform) and comparison steps. At step 650 a transformation is performed on at least one of the images (e.g., a transform matrix is applied to pixels of the image). One example of a technique of generating a transform matrix is described below with reference to FIGS. 8A and 8B.

Typically, after application of the transform, a pixel having coordinate (x',y') in a first image is transformed to a pixel having fractional coordinate (x/w,y/w) in a new perspective. Accordingly, after performing the transform, in some embodiments, an interpolation of pixel intensities may be used to achieve pixels having integer coordinates (x,y) in the new perspective (step 660). The interpolation step facilitates identification of corresponding pixels in the new perspective so that intensities of pixels corresponding to coordinates (x,y) can be compared. For example, intensities at locations between pixels (x/w,y/w) having integer coordinates (x,y) can be calculated using bilinear, bicubic, sinc, Fourier or Nurb interpolation.

Following performance of a transform to achieve intensity values of corresponding pixels, the images can be combined by comparing intensities of corresponding pixels to eliminate pixels that are affected by specular reflection. It will be appreciated that if, after transformation of the first image, the first image was not transformed into the perspective of the second image, a transform matrix would typically be applied to the second image such that the second image is transformed into the same perspective that the first image was transformed into. Accordingly, after the transformations, the first and second images correspond to a common perspective thereby facilitating comparison and combination of the first image and the second image.

An example of a comparison and combination technique is given as follows. First, corresponding pixels are identified (step 670) (i.e., pixels having a coordinate (x,y) in a same perspective are identified). Intensity values of the corresponding pixels are compared (step 680). For example, if the intensity of a given pixel in the first image I(x,y) is greater than the intensity of a corresponding pixel in the second image I'(x,y) by greater than a factor T then I(x,y) is assumed to be the result of specular reflection (690) and the intensity of the corresponding pixel in the third image R(x,y) is selected to be equal to I'(x,y) (step 699). Similarly, if the intensity of a given pixel in the second image I'(x,y) is greater than the intensity of a corresponding pixel in the first image I(x,y) by greater than a factor T, then I'(x,y) is assumed to be the result of specular reflection (690) and the intensity of the corresponding pixel in the third image R(x,y) is selected to be equal to I(x,y) (step 699). Factor T can be chosen to have any suitable value for example T≧1.25 or T≧2.0.

If neither the intensity of the pixel in the first image nor the intensity of the pixel in the second image is greater by a factor T (as determined in step 695), a selection of an intensity value R(x,y) for the corresponding pixel is performed. The corresponding pixel R(x,y) may be chosen using any of a number of different techniques (step 699). For example, the intensity R(x,y) can be chosen to be equal to the lesser of I(x,y) and I'(x,y). In some embodiments, the intensity is chosen to be the average of I(x,y) and I'(x,y). However, the intensity may be chosen to be the greater intensity of I(x,y) and I'(x,y) or any other suitable combination of intensity values I(x,y) and I'(x,y).

The comparison and combination of pixels as described above may be repeated for all of the pixels in the first and second images or only a subset of the pixels.

It will be appreciated that each image (e.g., each of an image from the first camera and an image from the second camera) comprises a cross sectional image of the eye and any image formed by the combination of images as described herein above typically results in a cross sectional image.

As with conventional slit scan apparatus, multiple cross sectional images from slits projected at multiple locations on an eye can be used to form two-dimensional or three-dimensional representations of the eye, where at least one of the cross sectional images is formed by combining two images to reduce the effects of specular reflection as described herein. Any suitable known or yet to be developed technique for forming a two-dimension image or a three-dimension image may be used to combine multiple images output from the present technique.

Although in some embodiments it is preferable that, in a plane perpendicular to the direction which the slit is projected, the two pathways pass through locations that are on a line parallel to a line extending along a width of the slit, such an arrangement is not necessary.

Figure 7:
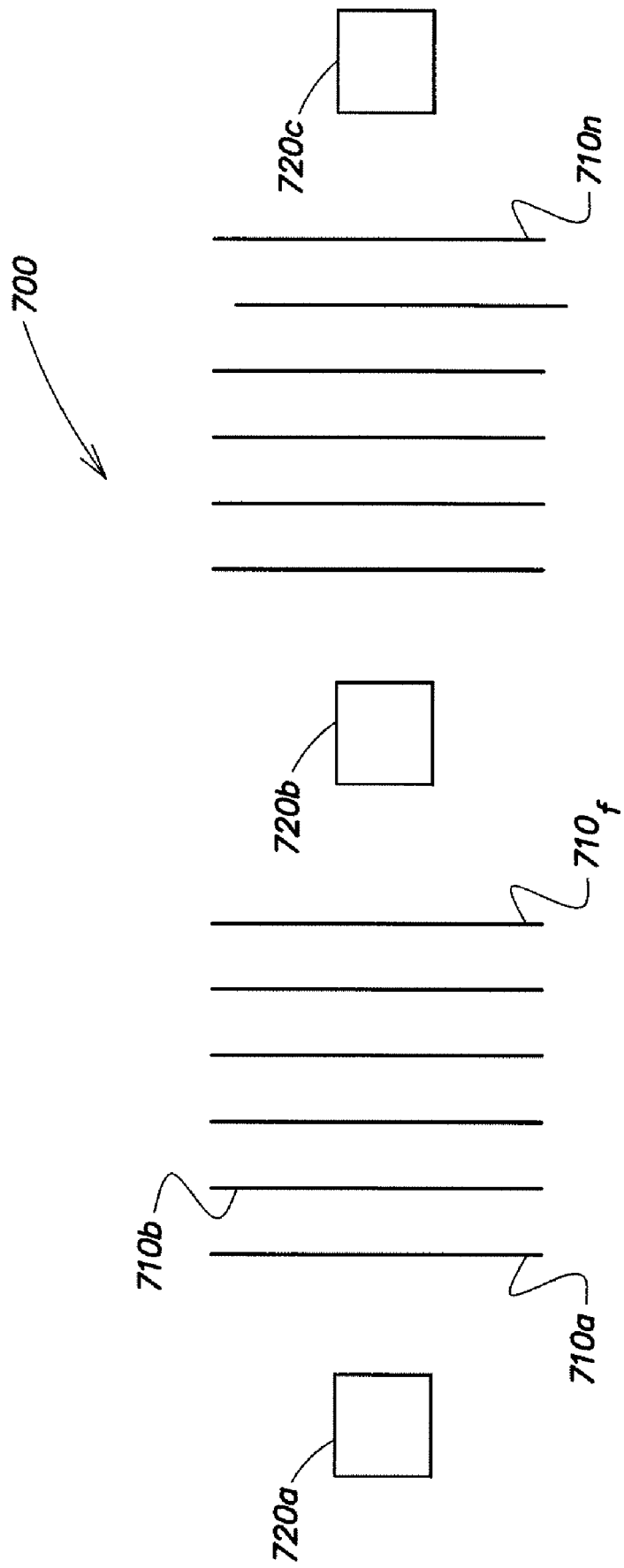
FIG. 7 is a schematic illustration of a front of another embodiment of an apparatus in which the cameras are asymmetrically disposed about a slit projectors.

Also, although in some embodiments it is advantageous that the cameras be symmetrically disposed about the paths of the slits of light, such an arrangement is not necessary. FIG. 7 shows an alternative embodiment of a measurement apparatus 700 in which slits of light are projected onto the eye from multiple locations 710a-710n that are translationally deviated from one another without angular deviation. It will be appreciated that transformations of pixels of images of light from the slits after they are scattered by an eye may be achieved such that corresponding pixels may be compared in the manner discussed above. Cameras located for example at two or more of locations 720a, 720b, 720c may be used to form the images of the eye from scattered slits of light. One or more cameras (e.g. camera 720b) may be located between the slits of light. It will be appreciated that a different transformation matrix may be calculated and used for slits of light projected from each of the various multiple locations to account for the positioning of the cameras relative to the slits. It will be appreciated that the pathways along which light from a slit at a first location (e.g., 710a) is imaged are different than the pathways along which light from a slit at another location (e.g., 710 b) is imaged.

In some embodiments in which data from two images is to be combined, and in which some of the data to be combined is disposed below the outer corneal surface of the eye, it may be desirable to account for refractive bending of the light as it passes through multiple media of the eye. It will be appreciated that such account can be made, for example, by measuring or assuming refractive index values for matter of the eye and accounting for the ray paths that the light travels to form an image on a sensor.

A matrix equation illustrating a transform capable of achieving a transformation of pixels (x',y') in an image according to aspects of the present invention is given in Equation 1.

$$\begin{vmatrix} a & b & c \\ d & e & f \\ g & h & i \end{vmatrix} \begin{vmatrix} x' \\ y' \\ 1 \end{vmatrix} = \begin{vmatrix} x \\ y \\ w \end{vmatrix}$$

Equation 1

Coefficients a-i in the matrix may be determined, for example, by imaging an object of known dimensions (e.g., sphere or a checkerboard test surface) located at a known location relative to a measurement apparatus, and determining the coefficients necessary to achieve an appropriate transformation result. It will be appreciated that coefficient i can be selected to have a value of 1 or a suitable normalization factor. It will be understood that although the above equation is a projective transform, under certain circumstances an affine transform may be used.

Figure 8A:
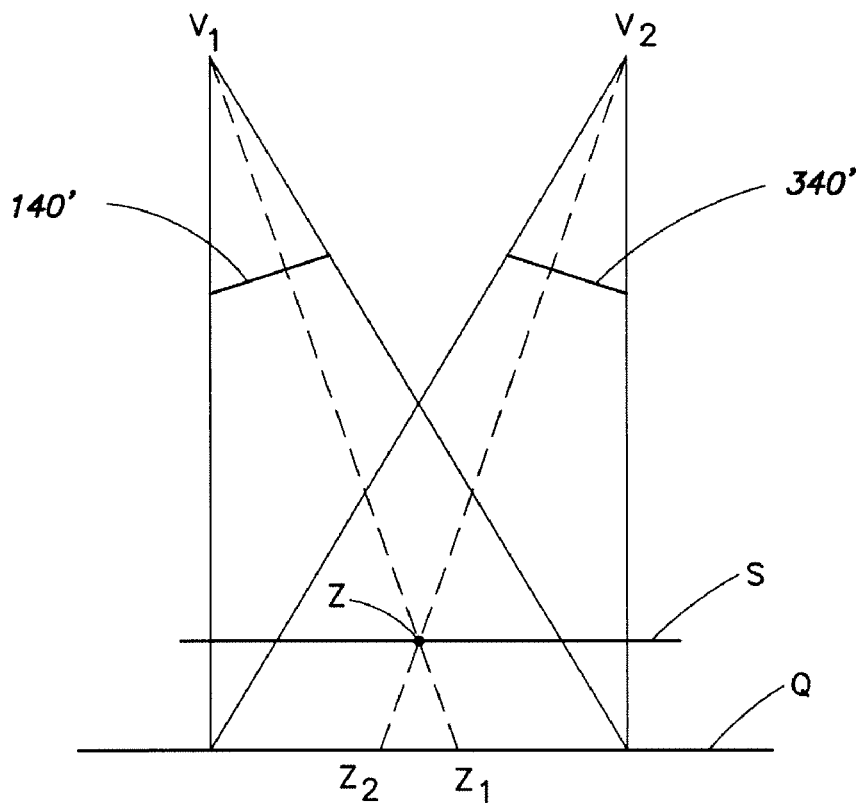
FIG. 8A is a schematic illustration of a relationship between a test surface having a known shape and a surface onto which projections of two image sensor surfaces are directed.
Figure 8B:
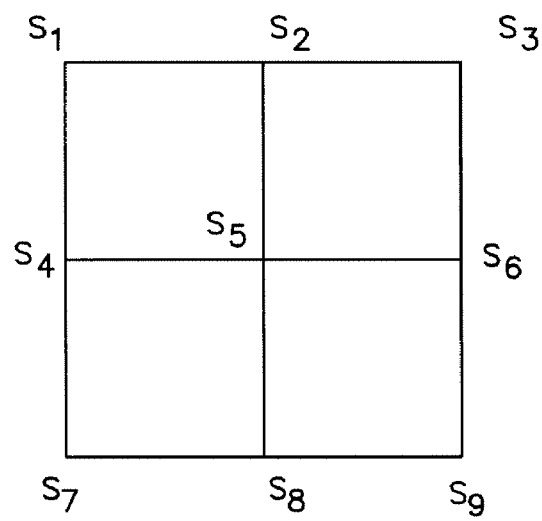
FIG. 8B is an example of a reference test surface having nine points of known location.

FIG. 8A schematically illustrates an example of a relationship between test surface S having an known shape such as a plane, Ax+By+Cz+D=0, and surface Q which contains a projection of the image sensor surfaces 140', 340' of cameras 142 and 342 (shown in FIG. 3) from vanishing points $V_1$ and $V_2$, respectively. A common point Z on the test surface will appear on the sensors at locations $Z_1$ and $Z_2$, respectively. For example, if test surface S is a grid (shown in FIG. 8B) having nine points $S_1$-$S_9$ of known locations, a first series of eight equations can be used to determine coefficients $a_1$-$h_1$ to form a first matrix that is capable of performing a projective transform on a pixel (x',y') from an image from sensor 142 into an alternative perspective, and a second series of eight equations can be used to determine coefficients $a_2$-$h_2$ to form a matrix that is capable of performing a projective transform of a pixel from an image from sensor 340 into the same alternative perspective.

For example, in some embodiments, the pixels from image sensor 140 can be transformed into the perspective of sensor 340. In such embodiments, the coefficients may be chosen such that an image of a given point (e.g., $S_1$) on sensor 140, after it is transformed, coincides with the location of the same given point ($S_1$) on image sensor 340. Using the transform matrix including coefficients $a_1$-$h_1$, pixels from cross sectional images obtained by sensors 140 (i.e., using slits of light) can be transformed into the perspective of sensor 340.

As stated above if, in a given embodiment, the transform matrix including coefficients $a_1$-h does not transform the first image into the perspective of the second image, a transform matrix including coefficients $a_2$-$h_2$, can be used to transform the pixels from cross sectional images obtained by sensors 340 into a common perspective with the images from sensor 140.

All of the pixels in a given cross sectional image or a subset of the pixels in a given image can be transformed. After transformation, pixels in the images can be compared and combined to reduce specular reflection in a manner as described above.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

What is claimed is:

1. An apparatus for measuring a subject's eye having an instrument axis, comprising:
   a slit projector for projecting slits of light;
   at least one sensor, the apparatus adapted to form a first image of light from a first slit on the at least one sensor after the light scatters from the eye along a first pathway, and the apparatus adapted to form a second image of light from the first slit on the at least one sensor after the light scatters from the eye along a second pathway;
   a processor operatively coupled to receive the first image and the second image, the processor adapted to perform a projective transformation of the second image and to combine data from the first image and the second image, after it is transformed, to form a third image.

2. The apparatus of claim 1, wherein the at least one sensor comprises: (A) a first sensor, the apparatus adapted to form the first image on the first sensor using light scattered along the first pathway, and (B) a second sensor, the apparatus adapted to form the second image on the second sensor using light scattered along the second pathway.

3. The apparatus of claim 1, wherein a second slit of the plurality of slits is projected at a different angle than the first slit,
   the apparatus being adapted to form a fourth image of light from the second slit on the at least one sensor after the light scatters from the eye along a third pathway, and the apparatus being adapted to form a fifth image of light from the second slit on the at least one sensor after the light scatters from the eye along a fourth pathway;
   the processor operatively coupled to receive the fourth image and the fifth image, the processor adapted to perform a projective transformation of the fourth image and to combine data from the fourth image, after it is transformed, and the fifth image to form a sixth image.

4. The apparatus of claim 1, wherein the at least one sensor comprises a single sensor, the apparatus comprising steering optics adapted to form the first image on the single sensor using light scattered along the first pathway, and the apparatus adapted to form the second image on the single sensor using light scattered along the second pathway.

5. The apparatus of claim 1, wherein the processor is adapted to perform a projective transformation of the first image prior to formation of the third image.

6. The apparatus of claim 1, wherein a second slit of the plurality of slits is translated without angular deviation relative to the first slit,
   the apparatus adapted to form a fourth image of light from the second slit on the at least one sensor after the light scatters from the eye along a third pathway, and the apparatus adapted to form a fifth image of light from the second slit on the at least one sensor after the light scatters from the eye along a fourth pathway;
   the processor operatively coupled to receive the fourth image and the fifth image, the processor adapted to perform a projective transformation of the fourth image and to combine data from the fourth image, after it is transformed, and the fifth image to form a sixth image.

7. The apparatus of claim 1, wherein the apparatus is adapted to acquire multiple cross sectional images formed using light from the plurality slits, and the processor is adapted to form a multidimensional representation of the eye from the multiple cross sectional images, wherein at least one of the cross sectional images is the third image.

* * * * *